(12) United States Patent
Fu et al.

(10) Patent No.: US 11,518,794 B2
(45) Date of Patent: Dec. 6, 2022

(54) SYNTHESIS METHOD FOR LIRAGLUTIDE WITH LOW RACEMATE IMPURITY

(71) Applicant: SHENZHEN JYMED TECHNOLOGY CO., LTD., Shenzhen (CN)

(72) Inventors: Yuqing Fu, Shenzhen (CN); Hongji Ma, Shenzhen (CN); Xinyu Li, Shenzhen (CN); Lixiang Zhang, Shenzhen (CN); Qin Zhi, Shenzhen (CN); Lifen Wu, Shenzhen (CN); Zicheng Liu, Shenzhen (CN)

(73) Assignee: SHENZHEN JYMED TECHNOLOGY CO., LTD., Shenzhen (CN)

( * ) Notice: Subject to any disclaimer, the term of this patent is extended or adjusted under 35 U.S.C. 154(b) by 963 days.

(21) Appl. No.: 16/326,265

(22) PCT Filed: Aug. 18, 2017

(86) PCT No.: PCT/CN2017/097970
§ 371 (c)(1),
(2) Date: Feb. 18, 2019

(87) PCT Pub. No.: WO2018/033127
PCT Pub. Date: Feb. 22, 2018

(65) Prior Publication Data
US 2019/0211073 A1 Jul. 11, 2019

(30) Foreign Application Priority Data

Aug. 19, 2016 (WO) ............... PCT/CN2016/096118

(51) Int. Cl.
*C07K 14/605* (2006.01)
*C07K 1/04* (2006.01)
*C07K 1/06* (2006.01)

(52) U.S. Cl.
CPC .............. *C07K 14/605* (2013.01); *C07K 1/04* (2013.01); *C07K 1/06* (2013.01)

(58) Field of Classification Search
CPC .......... C07K 1/04; C07K 1/06; C07K 1/1075; C07K 14/605
See application file for complete search history.

(56) References Cited

U.S. PATENT DOCUMENTS

| 9,260,474 | B2 | 2/2016 | Pan et al. | |
|---|---|---|---|---|
| 2014/0350219 | A1* | 11/2014 | Pan | C07K 1/1077 530/344 |
| 2018/0221451 | A1* | 8/2018 | Khopade | A61K 9/0019 |

FOREIGN PATENT DOCUMENTS

| CN | 102286092 A | 12/2011 |
|---|---|---|
| CN | 102731647 A | 10/2012 |
| CN | 103304659 A | 9/2013 |
| CN | 103408635 A | 11/2013 |
| CN | 103864918 A | 6/2014 |
| CN | 104004083 A | 8/2014 |
| CN | 104045705 A | 9/2014 |
| CN | 104045706 A | 9/2014 |
| CN | 104650219 A | 5/2015 |
| CN | 105732798 A | 7/2016 |
| CN | 106167521 A | 11/2016 |
| CN | 106478805 A | 3/2017 |
| CN | 106699871 A | 5/2017 |
| EP | 2757107 B1 | 7/2016 |
| WO | 2014147129 A1 | 9/2014 |
| WO | 2014199397 A2 | 12/2014 |
| WO | 2016046753 A1 | 3/2016 |
| WO | 2018032521 A1 | 2/2018 |

OTHER PUBLICATIONS

Machine translation of CN 105732798, published Jul. 6, 2016. (Year: 2016).*
Extended European Search Report for European Counterpart Application No. 17841099.9, dated Apr. 9, 2020 (7 pages).
Kuppanna, "Liraglutide synthesis by fragment method", ip.com Journal, ip.com Inc., XP013171970, ISSN: 1533-0001, Jun. 22, 2016, (10 pages).
Chinese Office Action for Chinese Counterpart Application No. 201780001586.5, dated Aug. 5, 2020 (16 pages).
International Search Report, and English Translation thereof, for International Application No. PCT/CN2017/097970, dated Nov. 14, 2017 (8 pages).
International Search Report, and English Translation thereof, for International Application No. PCT/CN2016/096118, dated May 11, 2017 (8 pages).

(Continued)

*Primary Examiner* — Jeffrey E. Russel
(74) *Attorney, Agent, or Firm* — Kagan Binder, PLLC

(57) ABSTRACT

A synthesis method for low-racemization impurity liraglutide comprises the following steps: performing synthesis to obtain a propeptide, coupling 2 to 5 peptides comprising Thr-Phe on the propeptide by using a solid-phase synthesis method; further, performing solid-phase synthesis to obtain a liraglutide resin; the liraglutide resin is cracked after modification, or the liraglutide resin is directly cracked, purified and frozen dry, so as to obtain the liraglutide. The provided liraglutide synthesis method effectively restrains or reduces the generation of racemization impurity D-Thr$^5$ highly similar to a product property, which facilitates the purification of the coarse liraglutide, and the high yield of the liraglutide is ensured, thereby greatly reducing production costs; during the synthesis of the liraglutide, the syntheses between dipeptide fragments, tripeptide fragments, the tetrapeptide fragments and pentapeptide fragments and the Gly-resin or the syntheses between the combination of the dipeptide fragments, the tripeptide fragments, the tetrapeptide fragments and pentapeptide fragments and the Gly resin can be carried out at the same time, and accordingly the synthesis time is shortened to some extent.

8 Claims, 4 Drawing Sheets

Specification includes a Sequence Listing.

(56) References Cited

OTHER PUBLICATIONS

"Palmitoyl Pentapeptide CAS 214047-00-4," retrieved from 'https://zspharmac.com/portfolio-item/palmitoyl-pentapeptide-cas-214047-00-4', on Jul. 4, 2022.

Viel et al., "Optimization of Automated Synthesis of Amide-Linked RNA", IACS Omega 2022, 7, 20420-20427.

\* cited by examiner

SYNTHESIS METHOD FOR LIRAGLUTIDE WITH LOW RACEMATE IMPURITY

CROSS REFERENCE TO RELATED APPLICATIONS

This application claims priority to International Application No. PCT/CN2017/097970 filed on Aug. 18, 2017, which claims priority to International Patent Application No. PCT/CN2016/096118, filed on Aug. 19, 2016, entitled "SYNTHESIS METHOD FOR LIRAGLUTIDE WITH LOW RACEMATE IMPURITY".

CROSS REFERENCE TO RELATED SEQUENCE LISTING

Also, the entire contents of the ASCII text file entitled "ACL0072US_Sequence_Listing" created on Dec. 16, 2021, having a size of 7 kilobytes is incorporated herein by reference.

TECHNICAL FIELD

The present disclosure relates to a method for synthesizing a polypeptide, and particularly to a method for synthesizing liraglutide with a low racemate impurity.

BACKGROUND

With the development of society, global incidence of diabetes, which has a significantly increasing trend, was estimated to be 2.8% in 2000 and is expected to be 4.3% by 2025, and the number of diabetics will increase from 171 million in 2000 to 380 million in 2025. Diabetes is divided into gestational diabetes, specific diabetes, type I diabetes, and type II diabetes. Type II diabetes, also known as non-insulin-dependent diabetes, is characterized by the fact that a human body itself can produce insulin, but cells are unable to respond to it, so that the effect of insulin is greatly compromised. There are many types of hypoglycemic agents for type II diabetes, including metformin, sulfonylureas, glucagon-like peptide-1 (GLP-1) receptor agonist, and the like. The GLP-1 receptor agonist is a hot topic in recent studies.

Liraglutide, one of human glucagon-like peptide-1 (GLP-1) analogues, with an English name Liraglutide, is a drug developed by Novo Nordisk in Denmark for the treatment of type II diabetes, and its injection was approved under a trade name Victoza by the FDA on Jan. 25, 2010, and approved by the SFDA on Mar. 4, 2011. As a GLP-1 receptor agonist, Liraglutide can play a good role in lowering blood glucose level.

At present, liraglutide is synthesized mainly by using a gene recombination technology and a stepwise coupling method. The synthesis of liraglutide, when is performed by the genetic recombination technique, has a relatively high technical difficulty and a relatively high cost, and an intermediate GLP-1(7-37)-OH needs to be repeatedly purified by HPLC and then reacted with Na-alkanoyl-Glu(ONSu)-OtBu under a liquid phase condition. Moreover, since the N-terminus of GLP-1(7-37)-OH is unprotected and the side chain protective groups of GLP-1(7-37)-OH are completely removed, many impurities are produced and Liraglutide is difficult to purify. As well known to those skilled in the art, the synthesis of liraglutide, when is performed by the stepwise coupling method, comprises: performing a condensation reaction of a resin as a solid phase carrier with Fmoc-Gly-OH to obtain Fmoc-Gly-resin; condensing, by solid-phase synthesis, amino acids with N-terminal Fmoc protection and side chain protection in sequence according to a main-chain peptide of liraglutide, wherein lysine is used in a form of Fmoc-Lys(X)-OH (X is a side chain protective group of Lys) or Fmoc-Lys (N-ε-(N-α-Palmitoyl-L-γ-glutamyl))-OH and each condensation reaction is performed for 30 min to 35 min; cleaving a side chain of lysine in a liraglutide resin after modification or directly cleaving the side chain of lysine in the liraglutide resin; and purifying and lyophilizing to obtain liraglutide. Due to a long sequence of liraglutide and a high proportion of hydrophobic amino acids, in stepwise coupling, β-sheet is easily formed, resulting in severe shrinkage of the resin and prolongation of the reaction time, and further producing, among the crude peptide, more racemate impurity, namely, $NH_2$—His-Ala-Glu-Gly-D-Thr-Phe-Thr-Ser-Asp-Val-Ser-Ser-Tyr-Leu-Glu-Gly-Gln-Ala-Ala-Lys(N-ε-(N-α-Palmitoyl-L-γ-glutamyl))-Glu-Phe-Ile-Ala-Trp-Leu-Val-Arg-Gly-Arg-Gly-COOH (D-Thr$^5$ liraglutide; SEQ ID NO:1), which has a property very close to that of the product, and making purification difficult; in addition, the resin shrinks severely and the reaction is incomplete, resulting in a lower yield.

On the one hand, the racemate by-product has a structure very similar to that of liraglutide, making much difficulty in purification and separation of the crude peptide of liraglutide, and no good effect can be achieved from separation although various purification separation systems have been tried. If multiple separations are performed, it can be foreseen that the separations will result in significant loss of the product. On the other hand, the racemate impurities have an adverse effect on the quality of the drug, namely, not only affecting stability and efficacy of the drug, but also being harmful to human health. Therefore, in the preparation process of synthesizing liraglutide, the production of racemate by-product should be minimized.

The main chain of liraglutide comprises 31 amino acids, and there are many forms of synthesis by fragment method, but only an appropriate fragment synthesizing method can ensure the production of less racemate by-product, and reduce the complexity of synthesis process, while guaranteeing the yield and purity of liraglutide. Through long-term experiments, inventors have surprisingly found that the synthesis of liraglutide using a method of the present disclosure allows a greatly reduced production of racemate impurity of liraglutide, namely, $NH_2$-His-Ala-Glu-Gly-D-Thr-Phe-Thr-Ser-Asp-Val-Ser-Ser-Tyr-Leu-Glu-Gly-Gln-Ala-Ala-Lys(N-ε-(N-α-Palmitoyl-L-γ-glutamyl))-Glu-Phe-Ile-Ala-Trp-Leu-Val-Arg-Gly-Arg-Gly-COOH (D-Thr$^5$ liraglutide; SEQ ID NO:1), the method is simple and the yield will not be lowered.

SUMMARY

It is an object of the present disclosure to provide a method for synthesizing liraglutide with a low racemate impurity.

A technical solution adopted by the present disclosure is:
a method for synthesizing liraglutide with a low racemate impurity including:
1) synthesizing to obtain a propeptide, and then coupling a 2~5 amino acid residue-containing peptide having Thr-Phe to the propeptide by using solid-phase synthesis; and
2) further performing a solid-phase synthesis to obtain a liraglutide resin, cleaving the liraglutide resin after side chain modification, or directly cleaving the liraglutide resin, purifying, and lyophilizing to give liraglutide.

As a further improvement of the aforementioned synthesis method, the 2~5 amino acid residue-containing peptide having Thr-Phe is selected from the group consisting of Thr-Phe, Gly-Thr-Phe, Thr-Phe-Thr, Gly-Thr-Phe-Thr (SEQ ID NO:2), Glu-Gly-Thr-Phe (SEQ ID NO:3), Thr-Phe-Thr-Ser (SEQ ID NO:4), Ala-Glu-Gly-Thr-Phe (SEQ ID NO:5), Glu-Gly-Thr-Phe-Thr (SEQ ID NO:6), Gly-Thr-Phe-Thr-Ser (SEQ ID NO:7), and Thr-Phe-Thr-Ser-Asp (SEQ ID NO:8).

As a further improvement of the aforementioned synthesis method, pentapeptide Glu-Phe-Ile-Ala-Trp (SEQ ID NO:9) is used during a process of synthesizing the propeptide.

As a further improvement of the aforementioned synthesis method, during a process of synthesizing liraglutide, a dipeptide fragment, a tripeptide fragment, a tetrapeptide fragment, a pentapeptide fragment or a combination thereof is coupled to an amino acid and a Fmoc-Gly-resin to obtain the liraglutide resin; wherein as a further improvement of the aforementioned synthesis method, the dipeptide fragment is selected from the group consisting of His-Ala, Ala-Glu, Glu-Gly, Thr-Ser, and Ala-Ala;

the tripeptide fragment is selected from the group consisting of Glu-Phe-Ile, Ser-Asp-Val, and Thr-Ser-Asp;

the tetrapeptide fragment is selected from the group consisting of Lys-Glu-Phe-Ile (SEQ ID NO:10) and Glu-Phe-Ile-Ala (SEQ ID NO:11);

the pentapeptide fragment is selected from the group consisting of Glu-Phe-Ile-Ala-Trp (SEQ ID NO:12), Ala-Lys-Glu-Phe-Ile (SEQ ID NO:13), Lys-Glu-Phe-Ile-Ala (SEQ ID NO:14), and Ala-Trp-Leu-Val-Arg (SEQ ID NO:15);

two peptide fragments are not used in combination when a same amino acid residue is present at respective ends of the two peptide fragments to be coupled with each other.

As a further improvement of the aforementioned synthesis method, the combination includes Ala-Trp-Leu-Val-Arg (SEQ ID NO:15), Ala-Lys-Glu-Phe-Ile (SEQ ID NO:13), Ser-Asp-Val, and Glu-Gly.

As a further improvement of the aforementioned synthesis method, the combination includes Glu-Phe-Ile-Ala-Trp (SEQ ID NO:12), Ala-Ala, Ser-Asp-Val, and Ala-Glu.

As a further improvement of the aforementioned synthesis method, the combination includes Ala-Trp-Leu-Val-Arg (SEQ ID NO:15), Glu-Phe-Ile, Thr-Ser-Asp, and Ala-Glu.

The beneficial effects of the present disclosure are as follows:

Through long-term experiments, inventors have surprisingly found that when a 2~5 amino acid residue-containing peptide with Thr-Phe, particularly one of a dipeptide Thr-Phe and tripeptides Gly-Thr-Phe and Thr-Phe-Thr, is used in the process of synthesizing liraglutide, the production of the racemate impurity of liraglutide i.e., D-Thr$^5$ liraglutide, can be greatly reduced, while ensuring that the yield will not be lowered.

The method for synthesizing liraglutide provided by the present disclosure effectively inhibits or reduces the production of the racemate impurity with very similar properties to the product, namely, D-Thr$^5$ liraglutide. In the crude peptide of liraglutide prepared, the racemate impurity D-Thr$^5$ liraglutide has an amount of less than 0.8% (w/w), which is advantageous for the purification of the crude peptide of liraglutide. In addition, The method of the present disclosure ensure a high yield and a greatly reduced production cost. In the process of synthesizing liraglutide, the synthesis of the dipeptide fragments, the tripeptide fragments, the tetrapeptide fragments, the pentapeptide fragments or combinations thereof with the Gly-resin can be carried out simultaneously, so that synthesis time is also shortened.

DETAILED DESCRIPTION OF THE EMBODIMENTS

Figure 1:
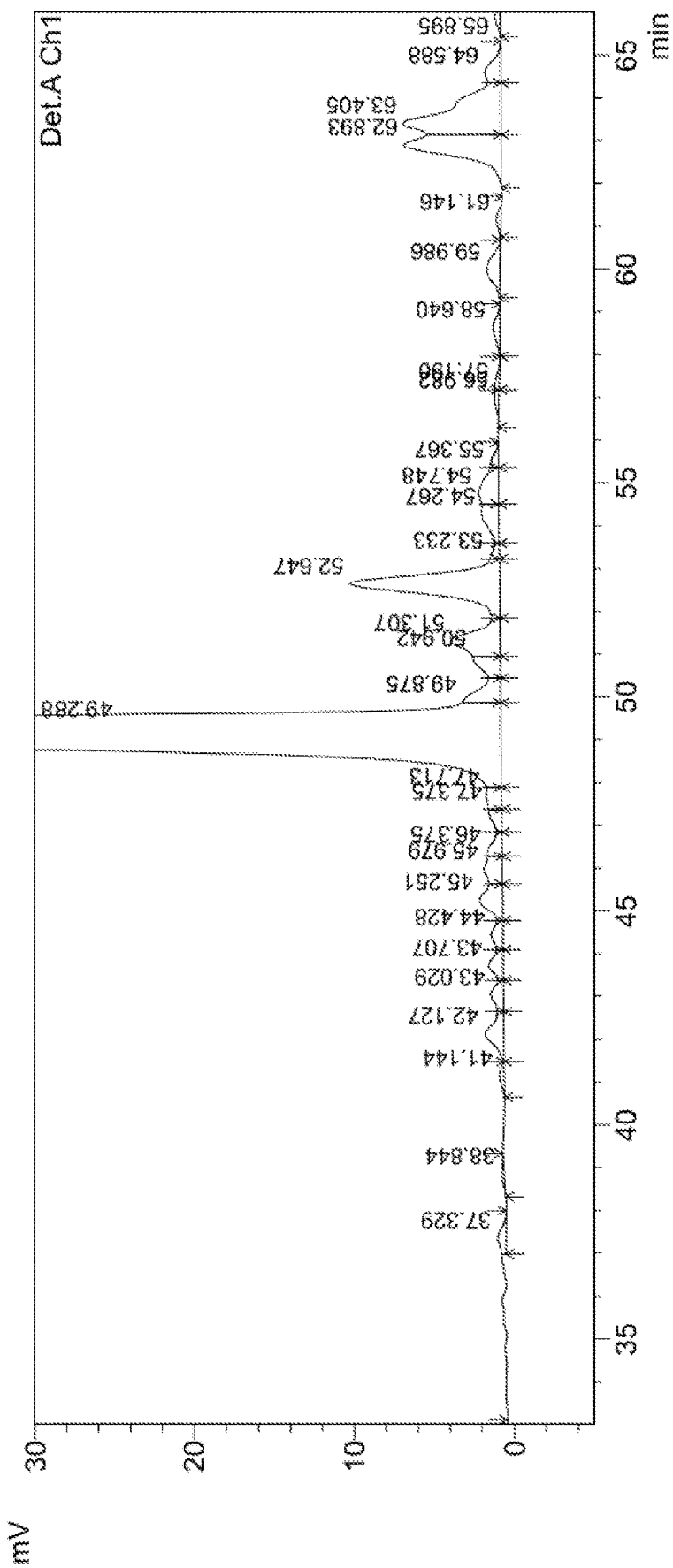
FIG. 1 shows an HPLC spectrum of a crude peptide of liraglutide prepared in example 1.

The method for synthesizing liraglutide of the present disclosure will be further described in detail below in conjunction with the specific examples so that those skilled in the art can further understand the present disclosure. The examples should not be construed as limiting the scope of protection.

Specific meanings of English abbreviations used are shown in Table 1.

TABLE 1

Specific meanings of the English abbreviations used in the specification and claims

| English abbreviation | Meaning | English abbreviation | Meaning |
| --- | --- | --- | --- |
| DIC | N,N'-diisopropylcarbodiimide | DIPEA | N,N'-diisopropylethylamine |
| HONb | N-hydroxy-5-norbornene-2,3-dicarboximide | HOBT | 1-hydroxybenzotriazole |
| DCC | N,N'-dicyclohexylcarbodiimide | TFA | trifluoroacetic acid |
| DCM | dichloromethane | EDT | ethanedithiol |
| Et$_2$O | diethyl ether | DMF | N,N'-dimethylformamide |
| 20% DBLK | 20% hexahydropyridine (v)/N,N'-dimethylformamide (v) | TFE | trifluoroethanol |
| | | Anisole | anisole |
| EA | ethyl acetate | TIS | triisopropylsilane |
| H$_2$O | water | THF | tetrahydrofuran |
| NaHCO$_3$ | sodium bicarbonate | PIP | hexahydropyridine |
| HBTU | benzotriazole-N,N,N',N'-tetramethyluronium hexafluorophosphate | DMAP | 4-dimethylaminopyridine |
| PyBOP | benzotriazol-1-yl-oxytripyrrolidinyl hexafluorophosphate | | |

Protective group is those commonly used in the field of amino acid synthesis for protecting a group, such as an amino group, a carboxyl group, and the like, in a main chain and a side chain of an amino acid from interfering with synthesis, it prevents the group, such as the amino group, the carboxyl group and the like, from reacting and forming an impurity during preparation of a target product. For amino acids in the present disclosure that need to protect side chains, those skilled in the art are well aware of their side chain structures and the use of common protective groups to protect groups, such as an amino group, a carboxyl group and the like, on the side chain of the amino acid. Preferably, in the present disclosure, the side chains of histidine and glutamine are protected by Trt-protective group, the side chains of glutamic acid and aspartic acid are protected by OtBu-protective group, the side chain of tryptophan is protected by Boc-protective group, the side chains of threonine, serine, and tyrosine are protected by tBu-protective group, the side chain of lysine is protected by Alloc-protective group, and the side chain of arginine is protected by Pbf-protective group. In addition, for amino acids involved in the method of the present disclosure, the N-terminus of the amino acids is preferably protected by a Fmoc-protective group, and histidine can also be protected by a Boc-protective group.

The amino acids or peptides used in the present disclosure, particularly the dipeptide, tripeptide, tetrapeptide, pentapeptide, and the like, can be protected by using a protective group according to the requirement of synthesis.

The propeptide herein refers to a polypeptide fragment synthesized from the C-terminus to the N-terminus of the liraglutide peptide sequence in the synthesis of liraglutide, and doesn't contain the 2~5 amino acid residue containing peptide having Thr-Phe. The protective group can be coupled to the side chain of the propeptide. The propeptide can be obtained by custom synthesis (purchase) or synthesized by a known method. In particular, the propeptide is obtained by solid phase peptide synthesis.

The structure of the racemate impurity among the crude peptide of liraglutide herein is $NH_2$—His-Ala-Glu-Gly-D-Thr-Phe-Thr-Ser-Asp-Val-Ser-Ser-Tyr-Leu-Glu-Gly-Gln-Ala-Ala-Lys(N-ε-(N-α-Palmitoyl-L-γ-glutamyl))-Glu-Phe-Ile-Ala-Trp-Leu-Val-Arg-Gly-Arg-Gly-COOH (SEQ ID NO:1), and is represented by D-Thr$^5$ liraglutide.

Example 1

1) 4.25 g of Fmoc-Gly-Wang resin (0.279 mmol/g) was added to a solid-phase reaction column, and washed twice with DMF. The resin was swelled with DMF for 30 min, deprotected with DBLK (5 min plus 7 min), and washed with DMF for 6 times. The ninhydrin test was positive.

2. Fmoc-Arg(pbf)-OH (3.245 g, 5 mmol) and HOBt (0.426 g, 3.15 mmol) were dissolved in 15 mL of DMF, and DIC (0.49 mL, 3.15 mmol) was added in an ice bath for activation for 5 minutes. The activated solution was added into the above solid-phase reaction column, and reacted under nitrogen for 2 h with stirring. The ninhydrin test was negative, and the Fmoc-Arg(pbf)-Gly-Wang resin was obtained. The reaction solution was drained. The resin was washed with DMF for 3 times, deprotected with DBLK (5 min plus 7 min), and washed with DMF for 6 times. The ninhydrin test was negative, and H-Arg(pbf)-Gly-Wang resin was obtained.

3. Fmoc-Gly-OH, Fmoc-Ala-Trp(Boc)-Leu-Val-Arg(Pbf)-OH (SEQ ID NO:16), Fmoc-Ala-Lys(Alloc)-Glu(OtBu)-Phe-Ile-OH (SEQ ID NO:17), Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Ser(tBu)-Asp(OtBu)-Val-OH, Fmoc-Thr(tBu)-OH, Fmoc-Thr(tBu)-Phe-OH, and Fmoc-Glu(OtBu)-Gly-OH were sequentially coupled to the H-Arg(pbf)-Gly-Wang resin.

4. Boc-His(Trt)-Ala-OH (2.89 g, 5 mmol) and HOBt (0.426 g, 3.15 mmol) were dissolved in 15 mL of DMF, and DIC (0.49 mL, 3.15 mmol) was added in an ice bath for activation for 5 minutes. The activated solution was added into the above solid-phase reaction column, and reacted under nitrogen for 2 h with stirring. The ninhydrin test was negative. The resin was washed with DMF for 4 times and washed with DCM twice.

5. To the above solid-phase reaction column, 15 mL of DCM and 1.08 g of phenylsilane were added, followed by 0.289 g of tetrakis(triphenylphosphine)palladium after stirring under nitrogen for 1 minute. The solution was reacted for 0.5 h, and then drained, and the resin was washed with DCM for 6 times. The ninhydrin test was positive.

6. Fmoc-Glu-OtBu (2.128 g, 5 mmol), HOBt (0.709 g, 5.25 mmol), and PyBOP (2.602 g, 5 mmol) were dissolved in 25 mL of DMF. DIPEA (1.75 mL, 10 mmol) was added in an ice bath for activation for 3 minutes. The activated solution was added into the above solid-phase reaction column, and reacted under nitrogen for 2 h with stirring. The ninhydrin test was negative. The solution was drained, and the resin was washed with DMF for 4 times and washed with DCM twice.

7) 20 mL of DCM and DIPEA (1.75 mL, 10 mmol) were added into the above solid-phase reaction column. After thoroughly stirring under nitrogen, palmitoyl chloride (1.374 g, 5 mmol) was slowly added dropwise. After adding, the reaction was continued for 2 h. The ninhydrin test was negative. The solution was drained. The resin was washed with DCM for 6 times, shrunk with MeOH, and dried in vacuo to obtain 9.43 g of peptide resin.

8) 9.43 g of the liraglutide resin obtained above was added into the mixed acid hydrolysate (containing 10 mL/g liraglutide resin) with a volume ratio of TFA:water:EDT=90:5:5. The reaction solution was stirred thoroughly, and reacted at room temperature for 3 h with stirring. The reaction mixture was filtered through a sand core funnel, and the filtrate was collected. The resin was washed with a small amount of TFA for three times. The filtrate was combined, and then concentrated in vacuo, and anhydrous ethyl ether was added for precipitation. Then, the precipitate was washed with anhydrous ethyl ether for three times, and the solution was drained to obtain an off-white powder. The off-white powder was dried in vacuo to a constant weight.

4.25 g of the crude peptide of liraglutide was obtained with a yield of 91.2% and a purity of 70.61%. The racemate impurity with a structure similar to that of liraglutide, i.e. D-Thr$^5$ liraglutide, was closely adjacent to the main peak, with a relative retention time of about 1.0 and an amount of 0.74%. The HPLC spectrum was shown in FIG. 1. The results of the retention time and peak area of characteristic peaks were shown in Table 2.

TABLE 2

Results of retention time and peak area of characteristic peaks of the crude peptide of liraglutide of example 1

| Ser. No. | Retention time (min) | Peak area (AU*s) | Peak area ratio % |
|---|---|---|---|
| 1 | 32.617 | 9624 | 0.14 |
| 2 | 37.329 | 16327 | 0.24 |
| 3 | 38.844 | 4797 | 0.07 |
| 4 | 41.144 | 9029 | 0.13 |
| 5 | 42.127 | 42365 | 0.62 |

TABLE 2-continued

Results of retention time and peak area of characteristic peaks of the crude peptide of liraglutide of example 1

| Ser. No. | Retention time (min) | Peak area (AU*s) | Peak area ratio % |
|---|---|---|---|
| 6 | 43.029 | 24319 | 0.36 |
| 7 | 43.707 | 26910 | 0.40 |
| 8 | 44.428 | 22402 | 0.33 |
| 9 | 45.251 | 49349 | 0.72 |
| 10 | 45.979 | 38278 | 0.56 |
| 11 | 46.375 | 21074 | 0.31 |
| 12 | 47.375 | 18961 | 0.28 |
| 13 | 47.713 | 27321 | 0.40 |
| 14 | 49.288 | 4809989 | 70.61 |
| 15 | 49.875 | 50079 | 0.74 |
| 16 | 50.942 | 38263 | 0.56 |
| 17 | 51.307 | 99047 | 1.45 |
| 18 | 52.647 | 292573 | 4.29 |
| 19 | 53.233 | 8892 | 0.13 |
| 20 | 54.267 | 39871 | 0.59 |
| 21 | 54.748 | 49558 | 0.73 |
| 22 | 55.367 | 8979 | 0.13 |
| 23 | 56.982 | 7451 | 0.11 |
| 24 | 57.190 | 6251 | 0.09 |
| 25 | 58.640 | 14643 | 0.21 |
| 26 | 59.986 | 30740 | 0.45 |
| 27 | 61.146 | 7473 | 0.11 |
| 28 | 62.893 | 185727 | 2.73 |
| 29 | 63.405 | 247896 | 3.64 |
| 30 | 64.588 | 29880 | 0.44 |
|  | 65.895 | 8106 | 0.12 |

Example 2

1) H-Arg(pbf)-Gly-Wang resin was synthesized according to the method of Example 1, and Fmoc-Gly-OH, Fmoc-Arg (pbf)-OH, Fmoc-Val-OH, Fmoc-Leu-OH, Fmoc-Glu (OtBu)-Phe-Ile-Ala-Trp(Boc)-OH (SEQ ID NO:18), Fmoc-Lys(Alloc)-OH, Fmoc-Ala-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Ser(tBu)-Asp(OtBu)-Val-OH, Fmoc-Thr(tBu)-OH, Fmoc-Thr(tBu)-Phe-OH, Fmoc-Gly-OH, and Fmoc-Ala-Glu(OtBu)-OH were sequentially coupled to the H-Arg(pbf)-Gly-Wang resin.

2. Boc-His(Trt)-OH (2.49 g, 5 mmol) and HOBt (0.426 g, 3.15 mmol) were dissolved in 15 mL of DMF, and DIC (0.49 mL, 3.15 mmol) was added in an ice bath for activation for 5 minutes. The activated solution was added into the solid-phase reaction column, and stirred under nitrogen for 2 h. The ninhydrin test was negative. The resin was washed with DMF for 4 times and washed with DCM twice. The remaining steps were referred to the steps 5-8 in example 1, and the product was dried in vacuo to a constant weight.

4.34 g of the crude peptide of liraglutide was obtained with a yield of 90.2% and a purity of 71.68%. The racemate impurity with a structure similar to that of liraglutide, i.e., D-Thr$^5$ liraglutide, was closely adjacent to the main peak, with a relative retention time of about 1.0 and an amount of 0.71%. The HPLC spectrum was similar to that shown in FIG. 1.

Example 3

1) 3.58 g of Fmoc-Gly-2-CTC resin (0.279 mmol/g) was added to a solid-phase reaction column, and washed twice with DMF. The resin was swelled with DMF for 30 min, deprotected with DBLK (5 min plus 7 min), and washed with DMF for 6 times. The ninhydrin test was positive.

2. Fmoc-Arg(pbf)-OH (3.245 g, 5 mmol) and HOBt (0.426 g, 3.15 mmol) were dissolved in 15 mL of DMF, and DIC (0.49 mL, 3.15 mmol) was added in an ice bath for activation for 5 minutes. The activated solution was added into the above solid-phase reaction column, and reacted under nitrogen for 2 h with stirring. The ninhydrin test was negative, and Fmoc-Arg(pbf)-Gly-2-CTC resin was obtained. The reaction solution was drained. The resin was washed with DMF for 3 times, deprotected with DBLK (5 min plus 7 min), and washed with DMF for 6 times. The ninhydrin test was negative, and H-Arg(pbf)-Gly-2-CTC resin was obtained.

3. Fmoc-Gly-OH, Fmoc-Ala-Trp(Boc)-Leu-Val-Arg (Pbf)-OH (SEQ ID NO:16), Fmoc-Glu(OtBu)-Phe-Ile-OH, Fmoc-Lys(N-ε-(Nα-Palmitoyl-L-γ-glutamyl-OtBu)), Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Thr(tBu)-Ser(tBu)-Asp(OtBu)-OH, Fmoc-Gly-Thr(tBu)-Phe-OH, Fmoc-Ala-Glu(OtBu)-OH, and Boc-His (Trt)-OH were sequentially coupled to the H-Arg(pbf)-Gly-2-CTC resin.

4. Boc-protective group was removed in 10 mL of 50% TFA/DCM solution per gram of the resin for 20 min. Then the resin was washed with DCM for 6 times, and dried in vacuo to obtain 9.21 g of peptide resin.

5. The peptide resin was added into a mixed acid hydrolysate (containing 10 mL/g liraglutide resin) with a volume ratio of TFA:Anisole:TIS:H$_2$O:EDT=92:2:2:2:2. The solution was stirred thoroughly, and reacted at room temperature for 3 h with stirring. The reaction mixture was filtered through a sand core funnel, and the filtrate was collected. The resin was washed with a small amount of TFA for three times. The filtrate was combined, and then concentrated in vacuo, and anhydrous ether was added for precipitation. Then, the precipitate was washed with anhydrous ethyl ether for three times, and the solution was drained to obtain an off-white powder. The off-white powder was dried in vacuo to a constant weight.

4.31 g of the crude peptide of liraglutide was obtained with a yield of 90.5% and a purity of 72.02%. The racemate impurity with a structure similar to that of liraglutide, i.e., D-Thr$^5$ liraglutide, was closely adjacent to the main peak, with a relative retention time of about 1.0 and an amount of 0.70%. The HPLC spectrum was similar to that shown in FIG. 1.

Example 4

H-Arg(pbf)-Gly-2-CTC resin was synthesized according to the method of Example 3, and Fmoc-Gly-OH, Fmoc-Ala-Trp(Boc)-Leu-Val-Arg(Pbf)-OH (SEQ ID NO:16), Fmoc-Glu(OtBu)-Phe-Ile-OH, Fmoc-Lys(N-ε-(Nα-Palmitoyl-L-γ-glutamyl-OtBu)), Fmoc-Ala-OH, Fmoc-Ala-OH, Fmoc-Gln (Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Ser(tBu)-Asp(OtBu)-Val-OH, Fmoc-Thr(tBu)-Phe-Thr(tBu)-OH, Fmoc-Glu(OtBu)-Gly-OH, and Boc-His(Trt)-Ala-OH were sequentially coupled to the H-Arg(pbf)-Gly-2-CTC resin. The remaining steps were referred to the steps 4-5 in example 3, and the product was dried in vacuo to a constant weight.

4.41 g of the crude peptide of liraglutide was obtained with a yield of 91.5% and a purity of 72.72%. The racemate impurity with a structure similar to that of liraglutide, i.e., D-Thr$^5$ liraglutide, was closely adjacent to the main peak, with a relative retention time of about 1.0 and an amount of 0.69%. The HPLC spectrum was similar to that shown in FIG. 1.

Example 5

H-Arg(pbf)-Gly-2-CTC resin was synthesized according to the method of example 3, and Fmoc-Gly-OH, Fmoc-Arg(Pbf)-OH, Fmoc-Val-OH, Fmoc-Leu-OH, Fmoc-Trp(Boc)-OH, Fmoc-Lys(Alloc)-Glu(OtBu)-Phe-Ile-Ala-OH (SEQ ID NO:19), Fmoc-Ala-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Thr(tBu)-Phe-Thr(tBu)-Ser(tBu)-OH (SEQ ID NO:20), Fmoc-Glu(OtBu)-Gly-OH, and Boc-His(Trt)-Ala-OH were sequentially coupled to the H-Arg(pbf)-Gly-2-CTC resin. The remaining steps were referred to the steps 4-5 in example 3, and the product was dried in vacuo to a constant weight.

4.50 g of the crude peptide of liraglutide was obtained with a yield of 91.8% and a purity of 70.72%. The racemate impurity with a structure similar to that of liraglutide, i.e., D-Thr$^5$ liraglutide, was closely adjacent to the main peak, with a relative retention time of about 1.0 and an amount of 0.70%. The HPLC spectrum was similar to that shown in FIG. 1.

Example 6

H-Arg(pbf)-Gly-2-CTC resin was synthesized according to the method of example 3, and Fmoc-Gly-OH, Fmoc-Ala-Trp(Boc)-Leu-Val-Arg(Pbf)-OH (SEQ ID NO:16), Fmoc-Lys(Alloc)-Glu(OtBu)-Phe-Ile-OH (SEQ ID NO:21), Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Gly-Thr(tBu)-Phe-Thr(tBu)-OH (SEQ ID NO:22), Fmoc-Glu(OtBu)-OH, and Boc-His(Trt)-Ala-OH were sequentially coupled to the H-Arg(pbf)-Gly-2-CTC resin. The remaining steps were referred to the steps 5-8 in example 1, and the product was dried in vacuo to a constant weight.

4.50 g of the crude peptide of liraglutide was obtained with a yield of 91.5% and a purity of 71.53%. The racemate impurity with a structure similar to that of liraglutide, i.e., D-Thr$^5$ liraglutide, was closely adjacent to the main peak, with a relative retention time of about 1.0 and an amount of 0.71%. The HPLC spectrum was similar to that shown in FIG. 1.

Example 7

H-Arg(pbf)-Gly-Wang resin was synthesized according to the method of example 1, and Fmoc-Gly-OH, Fmoc-Ala-Trp(Boc)-Leu-Val-Arg(Pbf)-OH (SEQ ID NO:16), Fmoc-Glu(OtBu)-Phe-Ile-OH, Fmoc-Lys(N-ε-(Nα-Palmitoyl-L-γ-glutamyl-OtBu)), Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Glu(OtBu)-Gly-Thr(tBu)-Phe-Thr(tBu)-OH (SEQ ID NO:23), and Boc-His(Trt)-Ala-OH were sequentially coupled to the H-Arg(pbf)-Gly-Wang resin. The remaining steps were referred to the steps 4-5 in example 3, and the product was dried in vacuo to a constant weight.

4.40 g of the crude peptide of liraglutide was obtained with a yield of 90.6% and a purity of 72.03%. The racemate impurity with a structure similar to that of liraglutide, i.e., D-Thr$^5$ liraglutide, was closely adjacent to the main peak, with a relative retention time of about 1.0 and an amount of 0.70%. The HPLC spectrum was similar to that shown in FIG. 1.

Example 8

H-Arg(pbf)-Gly-2-CTC resin was synthesized according to the method of example 3, and Fmoc-Gly-OH, Fmoc-Ala-Trp(Boc)-Leu-Val-Arg(Pbf)-OH (SEQ ID NO:16), Fmoc-Glu(OtBu)-Phe-Ile-OH, Fmoc-Lys(N-ε-(Nα-Palmitoyl-L-γ-glutamyl-OtBu)), Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Gly-Thr(tBu)-Phe-Thr(tBu)-Ser(tBu)-OH (SEQ ID NO:24), Fmoc-Glu(OtBu)-OH, and Boc-His(Trt)-Ala-OH were sequentially coupled to the H-Arg(pbf)-Gly-2-CTC resin. The remaining steps were referred to the steps 4-5 in Example 3, and the product was dried in vacuo to a constant weight.

4.52 g of the crude peptide of liraglutide was obtained with a yield of 90.8% and a purity of 70.36%. The racemate impurity having a structure similar to that of liraglutide, i.e., D-Thr$^5$ liraglutide, was closely adjacent to the main peak, with a relative retention time of about 1.0 and an amount of 0.71%. The HPLC spectrum was similar to that shown in FIG. 1.

Example 9. Preparation of Refined Peptide of Liraglutide

1) Water was added to the crude liraglutide obtained in Example 1, stirred, and adjusted to pH 8.5 with ammonia water until the crude liraglutide was completely dissolved. The solution was filtered through a 0.45 m microporous membrane and purified for use.

2. Purification was performed by high performance liquid chromatography, by a column (50 mm*250 mm) with 10 m reverse phase C18 chromatographic packing, a mobile phase system of 0.1% TFA/aqueous solution −0.1% TFA/acetonitrile solution, and a flow rate of 90 mL/min for purification. Purification was performed by gradient system elution and cyclic sampling. A solution of the crude product was added to the column, and elution was run with a mobile phase. The main peak was collected, and acetonitrile was evaporated to obtain a concentrated solution of a purified intermediate of liraglutide. The concentrated solution of the purified intermediate of liraglutide was filtered through 0.45 μm microporous membrane for use.

3. Salt exchange was performed by high performance liquid chromatography, by a mobile phase system of 1% acetic acid/aqueous solution acetonitrile, a column (77 mm*250 mm) with 10 m reverse phase C18 chromatographic packing, and a flow rate of 90 mL/min for purification. The process was performed by gradient system elution and cyclic sampling. The sample was added to the column, and elution was run with a mobile phase. Spectrum was acquisited and changes in absorbance was observed. The salt-exchanged main peak was collected and detected for purity by analytical liquid phase. The solution of salt-exchanged main peak was combined and concentrated in vacuo to obtain an aqueous acetic acid solution of liraglutide for use.

4. Purification and then desalting was performed by HPLC. The chromatographic column was set as follows:

stationary phase: octadecylsilane-bonded silica gel; diameter and length of the column: 150 mm×250 mm; phase A: aqueous solution of 0.06% ammonia water; phase B: chromatographic grade acetonitrile; flow rate: 480 ml/min; gradient: 32% B-65% B; detection wavelength: 275 nm. The purified solution was concentrated by rotary evaporation, and lyophilized.

Figure 2:
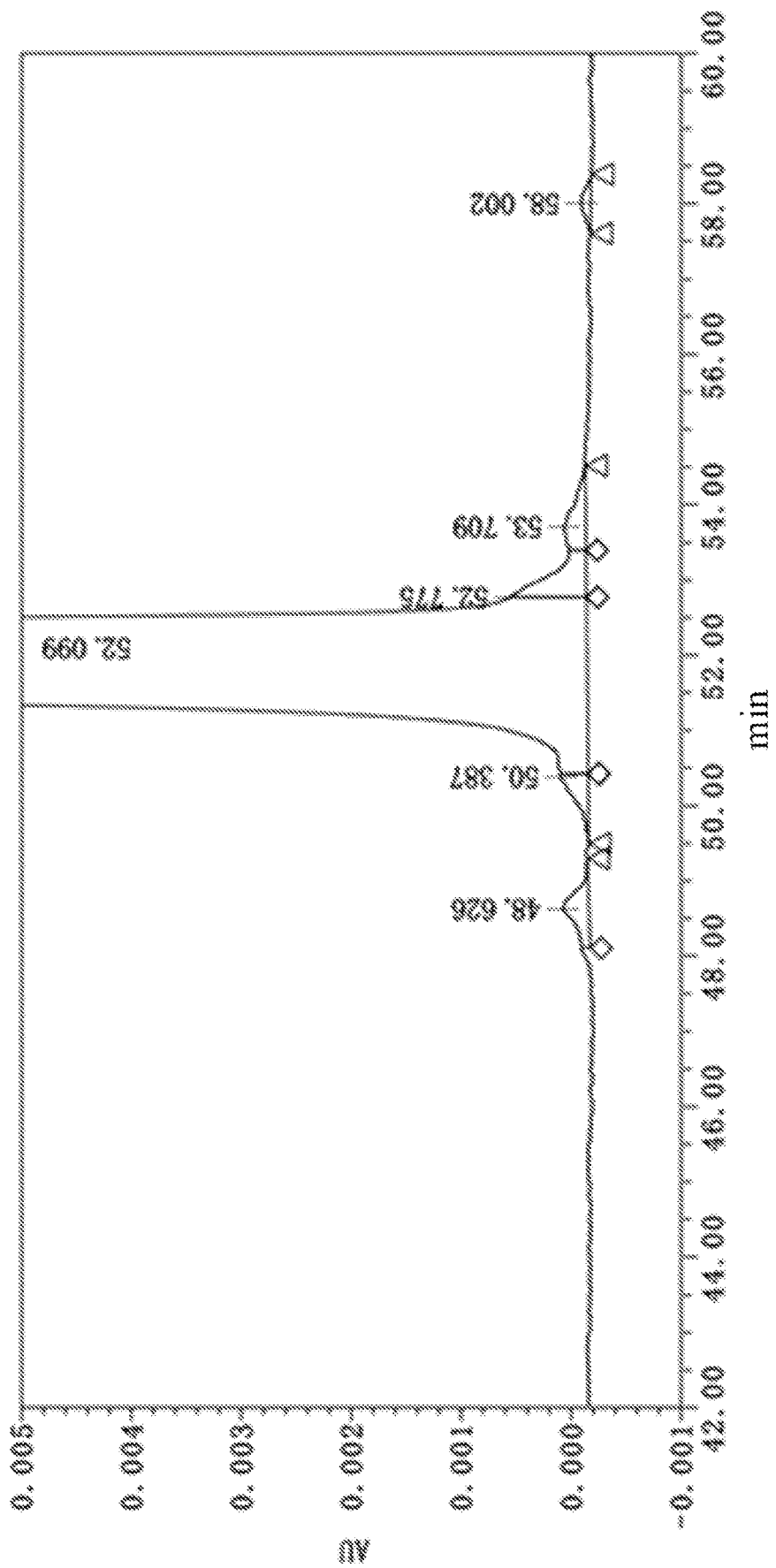
FIG. 2 shows an HPLC spectrum of a refined peptide of liraglutide prepared in example 9.

1.17 g of the pure product of liraglutide was obtained with a purity of 99.27% and a total yield of 25.12%. The racemate impurity with a structure similar to that of liraglutide, i.e., D-Thr$^5$ liraglutide, was closely adjacent to the main peak, with a relative retention time of about 1.0 and an amount of 0.27%. The HPLC spectrum was shown in FIG. 2. The results of the retention time and peak area of characteristic peaks were shown in Table 3.

TABLE 3

Results of retention time and peak area of characteristic peaks of liraglutide of Example 9

| Ser. No. | Retention time (min) | Peak area (AU*s) | Peak area ratio % |
|---|---|---|---|
| 1 | 48.626 | 7474 | 0.15 |
| 2 | 50.387 | 5525 | 0.11 |
| 3 | 52.099 | 4908123 | 99.27 |
| 4 | 52.775 | 13237 | 0.27 |
| 5 | 53.709 | 7596 | 0.15 |
| 6 | 58.002 | 2237 | 0.05 |

Example 10. Preparation of Refined Peptide of Liraglutide

The crude peptide of liraglutide prepared in Example 2 was purified by the same purification method as in Example 9.

1.15 g of the pure product of liraglutide was obtained with a purity of 99.31% and a total yield of 23.14%. The racemate impurity with a structure similar to that of liraglutide, i.e., D-Thr$^5$ liraglutide, was closely adjacent to the main peak, with a relative retention time of about 1.0 and an amount of 0.25%. The HPLC spectrum was similar to that shown in FIG. 2.

Example 11. Preparation of Refined Peptide of Liraglutide

The crude peptide of liraglutide prepared in Example 3 was purified by the same purification method as that in Example 9.

1.16 g of the pure product of liraglutide was obtained with a purity of 99.23% and a total yield of 24.14%. The racemate impurity with a structure similar to that of liraglutide, i.e., D-Thr$^5$ liraglutide, was closely adjacent to the main peak, with a relative retention time of about 1.0 and an amount of 0.26%. The HPLC spectrum was similar to that shown in FIG. 2.

Example 12. Preparation of Refined Peptide of Liraglutide

The crude peptide of liraglutide prepared in Example 4 was purified by the same purification method as that in Example 9.

1.19 g of the pure product of liraglutide was obtained with a purity of 99.36% and a total yield of 24.36%. The racemate impurity with a structure similar to that of liraglutide, i.e., D-Thr$^5$ liraglutide, was closely adjacent to the main peak, with a relative retention time of about 1.0 and an amount of 0.27%. The HPLC spectrum was similar to that shown in FIG. 2.

Example 13. Preparation of Refined Peptide of Liraglutide

The crude peptide of liraglutide prepared in Example 5 was purified by the same purification method as that in Example 9.

1.23 g of the pure product of liraglutide was obtained with a purity of 99.48% and a total yield of 25.14%. The racemate impurity with a structure similar to that of liraglutide, i.e., D-Thr$^5$ liraglutide, was closely adjacent to the main peak, with a relative retention time of about 1.0 and an amount of 0.26%. The HPLC spectrum was similar to that shown in FIG. 2.

Example 14. Preparation of Refined Peptide of Liraglutide

The crude peptide of liraglutide prepared in Example 6 was purified by the same purification method as that in Example 9.

1.21 g of the pure product of liraglutide was obtained with a purity of 99.50% and a total yield of 24.65%. The racemate impurity with a structure similar to that of liraglutide, i.e., D-Thr$^5$ liraglutide, was closely adjacent to the main peak, with a relative retention time of about 1.0 and an amount of 0.27%. The HPLC spectrum was similar to that shown in FIG. 2.

Example 15. Preparation of Refined Peptide of Liraglutide

The crude peptide of liraglutide prepared in Example 7 was purified by the same purification method as that in Example 9.

1.14 g of the pure product of liraglutide was obtained with a purity of 99.51% and a total yield of 23.46%. The racemate impurity with a structure similar to that of liraglutide, i.e., D-Thr$^5$ liraglutide, was closely adjacent to the main peak, with a relative retention time of about 1.0 and an amount of 0.26%. The HPLC spectrum was similar to that shown in FIG. 2.

Example 16. Preparation of Refined Peptide of Liraglutide

The crude peptide of liraglutide prepared in Example 8 was purified by the same purification method as that in Example 9.

1.21 g of the pure product of liraglutide was obtained with a purity of 99.48% and a total yield of 24.12%. The racemate impurity with a structure similar to that of liraglutide, i.e., D-Thr$^5$ liraglutide, was closely adjacent to the main peak, with a relative retention time of about 1.0 and an amount of 0.25%. The HPLC spectrum was similar to that shown in FIG. 2.

Comparative Example 1. Preparation of Crude Peptide of Liraglutide 1) 4.25 g of Fmoc-Gly-Wang resin (0.279 mmol/g) was added to a solid-phase reaction column, and washed twice with DMF. The resin was swelled with DMF for 30 min, deprotected with DBLK (5 min plus 7 min), and washed with DMF for 6 times. The ninhydrin test was positive.

2. Fmoc-Arg(pbf)-OH (3.245 g, 5 mmol) and HOBt (0.426 g, 3.15 mmol) were dissolved in 15 mL of DMF, and DIC (0.49 mL, 3.15 mmol) was added in an ice bath for activation for 5 minutes. The activated solution was added into the above solid-phase reaction column, and reacted under nitrogen for 2 h with stirring. The ninhydrin test was negative, and Fmoc-Arg(pbf)-Gly-Wang resin was obtained. The reaction solution was drained. The resin was washed with DMF for 3 times, deprotected with DBLK (5 min plus 7 min), and washed with DMF for 6 times. The ninhydrin test was negative, and H-Arg(pbf)-Gly-Wang resin was obtained.

3. Fmoc-Gly-OH, Fmoc-Arg(Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Alloc)-OH, Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, and Boc-His(Trt)-OH were sequentially coupled to the H-Arg(pbf)-Gly-Wang resin according to the above Fmoc-Arg(pbf)-OH coupling method.

4) 15 mL of DCM and 1.08 g of phenylsilane were added to the above solid-phase reaction column, followed by 0.289 g of tetrakis(triphenylphosphine)palladium after stirring under nitrogen for 1 minute. The solution was reacted for 0.5 h, drained, and the resin was washed with DCM for 6 times. The ninhydrin test was positive.

5. Fmoc-Glu-OtBu (2.128 g, 5 mmol), HOBt (0.709 g, 5.25 mmol), and PyBOP (2.602 g, 5 mmol) were dissolved in 25 mL of DMF, and DIPEA (1.75 mL, 10 mmol) was added in an ice bath for activation for 3 minutes. The activated solution was added into the above solid-phase reaction column, and reacted under nitrogen for 2 h with stirring. The ninhydrin test was negative. The solution was drained, and the resin was washed with DMF for 4 times and washed with DCM twice.

6) 20 mL of DCM and DIPEA (1.75 mL, 10 mmol) were added into the above solid-phase reaction column. After thoroughly stirring under nitrogen, palmitoyl chloride (1.374 g, 5 mmol) was slowly added dropwise. After adding, the reaction was continued for 2 h. The ninhydrin test was negative. The solution was drained. The resin was washed with DCM for 6 times, shrunk with MeOH, and dried in vacuo to obtain 7.46 g of peptide resin.

7. A mixed acid hydrolysate (containing 10 mL/g liraglutide resin) having a volume ratio of TFA:water:EDT=90:5:5 was added to a round-bottom flask with 7.46 g of the peptide resin of liraglutide. The solution was stirred thoroughly, and reacted at room temperature for 3 h with stirring. The reaction mixture was filtered through a sand core funnel, and the filtrate was collected. The resin was washed with a small amount of TFA for three times. The filtrates were combined, and then concentrated in vacuo, and anhydrous ethyl ether was added for precipitation. Then, the precipitate was washed with anhydrous ethyl ether for three times, and the solution was drained to obtain an off-white powder. The off-white powder was dried in vacuo to a constant weight to obtain 3.68 g of the crude peptide of liraglutide.

Figure 3:
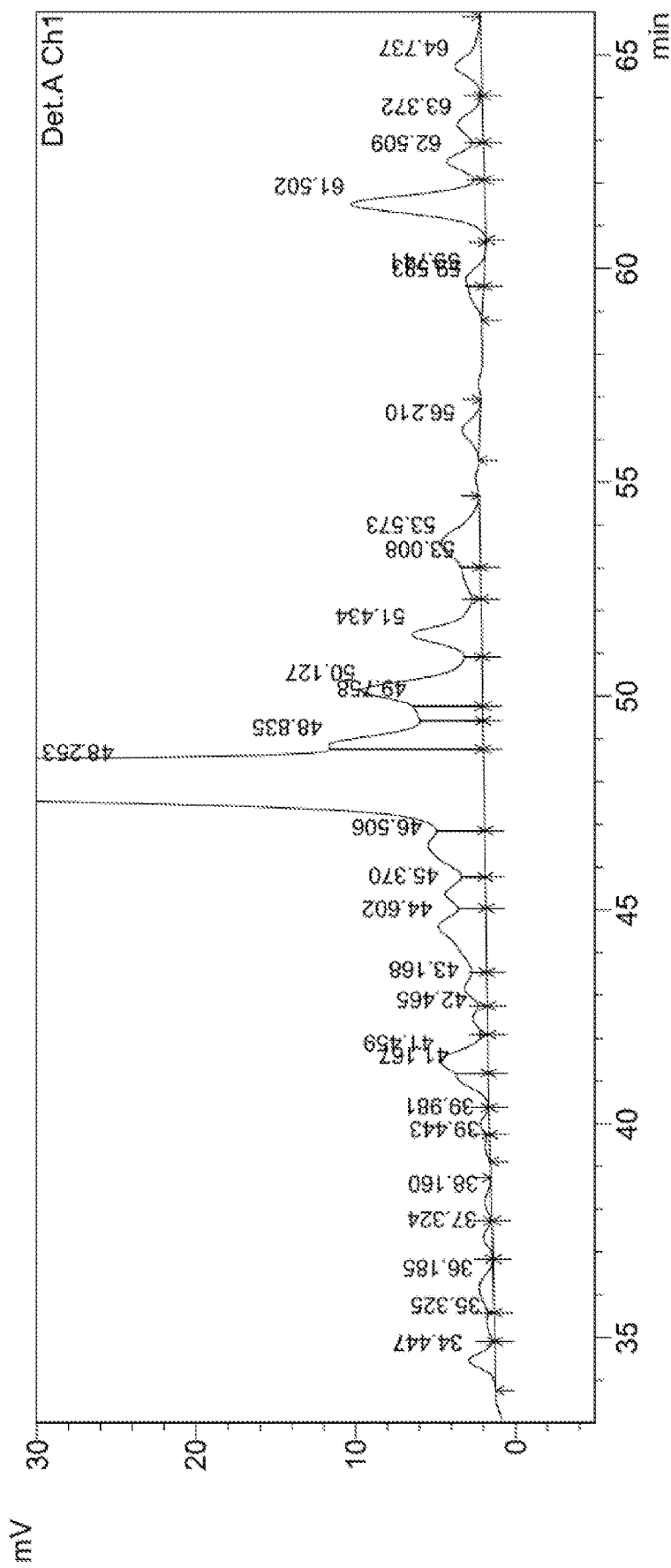
FIG. 3 shows an HPLC spectrum of a crude peptide of liraglutide prepared in comparative example 1.

The crude peptide of liraglutide has a yield of 80.5% and a purity of 68.63%. The racemate impurity with a structure similar to that of liraglutide, i.e., D-Thr$^5$ liraglutide, was closely adjacent to the main peak, with a relative retention time of about 1.0 and an amount of 2.39%. The HPLC spectrum was shown in FIG. 3. The results of the retention time and peak area of characteristic peaks were shown in Table 4.

TABLE 4

Results of retention time and peak area of characteristic peaks of the crude peptide of liraglutide of Comparative Example 1

| Ser. No. | Retention time (min) | Peak area (AU*s) | Peak area ratio % |
|---|---|---|---|
| 1 | 34.447 | 43379 | 0.39 |
| 2 | 35.325 | 13387 | 0.12 |
| 3 | 36.185 | 40142 | 0.36 |
| 4 | 37.324 | 14414 | 0.13 |
| 5 | 38.160 | 12441 | 0.11 |
| 6 | 39.443 | 7592 | 0.07 |
| 7 | 39.981 | 13136 | 0.12 |
| 8 | 41.167 | 45452 | 0.41 |
| 9 | 41.459 | 105145 | 0.94 |
| 10 | 42.465 | 27602 | 0.25 |
| 11 | 43.168 | 51138 | 0.46 |
| 12 | 44.602 | 178039 | 1.59 |
| 13 | 45.370 | 92060 | 0.82 |
| 14 | 46.506 | 182605 | 1.64 |
| 15 | 48.253 | 7661983 | 68.63 |
| 16 | 48.835 | 266500 | 2.39 |
| 17 | 49.758 | 87000 | 0.78 |
| 18 | 50.127 | 290537 | 2.60 |
| 19 | 51.434 | 166104 | 1.49 |
| 20 | 53.008 | 41115 | 0.37 |
| 21 | 53.573 | 129362 | 1.16 |
| 22 | 56.210 | 38923 | 0.35 |
| 23 | 59.583 | 24725 | 0.22 |
| 24 | 59.741 | 29094 | 0.26 |
| 25 | 61.502 | 269424 | 2.41 |
| 26 | 62.509 | 76005 | 0.68 |
| 27 | 63.372 | 58826 | 0.53 |
| 28 | 64.737 | 63926 | 0.57 |

Comparative Example 2. Preparation of Crude Peptide of Liraglutide 1) 3.58 g of Fmoc-Gly-2-CTC resin (0.279 mmol/g) was added to a solid-phase reaction column, and washed twice with DMF. The resin was swelled with DMF for 30 min, deprotected with DBLK (5 min plus 7 min), and washed with DMF for 6 times. The ninhydrin test was positive.

2. Fmoc-Arg(pbf)-OH (3.245 g, 5 mmol) and HOBt (0.426 g, 3.15 mmol) were dissolved in 15 mL of DMF, and DIC (0.49 mL, 3.15 mmol) was added in an ice bath for activation for 5 minutes. The activated solution was added into the above solid-phase reaction column, and reacted under nitrogen for 2 h with stirring. The ninhydrin test was negative, and Fmoc-Arg(pbf)-Gly-2-CTC resin was obtained. The reaction solution was drained. The resin was washed with DMF for 3 times, deprotected with DBLK (5 min plus 7 min), and washed with DMF for 6 times. The ninhydrin test was negative, and H-Arg(pbf)-Gly-2-CTC resin was obtained.

3. Fmoc-Gly-OH, Fmoc-Arg(Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(N-ε-(Nα-Palmitoyl-L-γ-glutamyl-OtBu)), Fmoc-Ala-OH, Fmoc-Ala-OH, Fmoc-Gln(Trt)-OH, Fmoc-Gly-OH, Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH, and Boc-His(Trt)-OH were sequentially coupled to the H-Arg(pbf)-Gly-Wang resin.

4. Boc-protective group was removed in 10 mL of 50% TFA/DCM solution per gram of the resin for 20 min, and then the resin was washed with DCM for 6 times, and dried in vacuo to obtain 8.52 g of peptide resin.

5. A mixed acid hydrolysate (containing 10 mL/g liraglutide resin) with a volume ratio of TFA:Anisole:TIS:H$_2$O:EDT=92:2:2:2:2 was added to a round-bottom flask with 8.52 g of the peptide resin of liraglutide. The solution was stirred thoroughly, and reacted at room temperature for 3 h with stirring. The reaction mixture was filtered through a sand core funnel, and the filtrate was collected. The resin was washed with a small amount of TFA for three times. The filtrate was combined, and then concentrated in vacuo, and anhydrous ethyl ether was added for precipitation. Then, the precipitate was washed with anhydrous ethyl ether for three times, and the solution was drained to obtain an off-white powder. The off-white powder was vacuum dried in vacuo to a constant weight and 3.68 g of the crude peptide of liraglutide was obtained.

The crude peptide of liraglutide has a yield of 79.8% and a purity of 68.61%. The racemate impurity with a structure similar to that of liraglutide, i.e., D-Thr$^5$ liraglutide, was closely adjacent to the main peak, with a relative retention time of about 1.0 and an amount of 2.40%. The HPLC spectrum was similar to that of FIG. 3.

As can be seen from the HPLC spectra and the corresponding data of examples 1-8 and comparative examples 1 and 2, the peak of racemate impurity, i.e., the peak of D-Thr$^5$ liraglutide, was closely adjacent to the main peak of liraglutide. Their retention times were 49.288 min and 49.875 min in example 1, respectively and were 48.253 min and 48.835 min in comparative example 1, respectively. The relative retention time of D-Thr$^5$ liraglutide was about 1.0, which was far from the requirement of separation. If D-Thr$^5$ liraglutide is present in a large amount, it will be very difficult to purify and separate the crude peptide. However, compared with comparative examples 1 and 2, the amount of D-Thr$^5$ liraglutide was reduced from respective 2.39% and 2.40% to 0.74% in example 1, relatively reducing by 69.04% and 69.17%, respectively. Compared with comparative examples 1 and 2, the amount of D-Thr$^5$ liraglutide was reduced from respective 2.39% and 2.40% to 0.71% in example 2, relatively reducing by 70.29% and 70.42%, respectively. Compared with comparative examples 1 and 2, the amount of D-Thr$^5$ liraglutide was reduced from respective 2.39% and 2.40% to 0.70% in example 3, relatively reducing by 70.71% and 70.83%, respectively. Compared with comparative examples 1 and 2, the amount of D-Thr$^5$ liraglutide was reduced from respective 2.39% and 2.40% to 0.69% in example 4, relatively reducing by 71.13% and 71.25%, respectively. Compared with comparative examples 1 and 2, the amount of D-Thr$^5$ liraglutide was reduced from respective 2.39% and 2.40% to 0.70% in example 5, relatively reducing by 70.71% and 70.93%, respectively. Compared with comparative examples 1 and 2, the amount of D-Thr$^5$ liraglutide was reduced from respective 2.39% and 2.40% to 0.71% in example 6, relatively reducing by 70.29% and 70.42%, respectively. Compared with comparative examples 1 and 2, the amount of D-Thr$^5$ liraglutide was reduced from respective 2.39% and 2.40% to 0.70% in example 7, relatively reducing by 70.71% and 70.93%, respectively. Compared with comparative examples 1 and 2, the amount of D-Thr$^5$ liraglutide was reduced from respective 2.39% and 2.40% to 0.71% in example 8, relatively reducing by 70.29% and 70.42%, respectively. It can be seen from the above that the method for synthesizing liraglutide provided in the present disclosure can greatly reduce the amount of the racemate impurity, i.e., D-Thr$^5$ liraglutide, which produced in the synthesis of the crude peptide of liraglutide. D-Thr$^5$ liraglutide is in an amount of less than 0.8%, which is very advantageous for purification.

In addition, liraglutide in example 1 has a yield of 91.2% and a purity of 70.61%, which were 10.7% and 1.98% higher than those of comparative example 1, respectively, and were 11.4% and 2.0% higher than those of comparative example 2, respectively. Liraglutide in example 2 has a yield of 90.2% and a purity of 71.68%, which were 9.7% and 3.05% higher than those of comparative example 1, respectively, and were 10.4% and 3.07% higher than those of comparative example 2, respectively. Liraglutide in example 3 has a yield of 90.5% and a purity of 72.02%, which were 10.0% and 3.39% higher than those of comparative example 1, respectively, and were 10.7% and 3.41% higher than those of comparative example 2, respectively. Liraglutide in example 4 has a yield of 91.5% and a purity of 72.72%, which were 11.0% and 4.09% higher than those of comparative example 1, respectively, and were 11.7% and 4.11% higher than those of comparative example 2, respectively. Liraglutide in example 5 has a yield of 91.8% and a purity of 70.72%, which were 11.3% and 2.09% higher than those of comparative example 1, respectively, and were 12.0% and 2.11% higher than those of comparative example 2, respectively. Liraglutide in example 6 has a yield of 91.5% and a purity of 71.53%, which were 11.0% and 2.9% higher than those of comparative example 1, respectively, and were 11.7% and 2.92% higher than those of comparative example 2, respectively. Liraglutide in example 7 has a yield of 90.6% and a purity of 72.03%, which were 10.1% and 3.40% higher than those of comparative example 1, respectively, and were 10.8% and 3.42% higher than those of comparative example 2, respectively. Liraglutide in example 8 has a yield of 90.8% and a purity of 70.36%, which were 10.3% and 1.73% higher than those of comparative example 1, respectively, and were 11.0% and 1.75% higher than those of comparative example 2, respectively. It can be seen that the method for synthesizing liraglutide provided by the present disclosure can improve the yield and purity of the crude peptide of liraglutide, which is advantageous for purification.

The method of the present disclosure can greatly reduce the racemate impurity, i.e., D-Thr$^5$ liraglutide which produced during the synthesis of liraglutide, while the yield is not lowered. It is advantageous for purifying the crude peptide of liraglutide to obtain the refined peptide.

Comparative Example 3. Preparation of Refined Peptide of Liraglutide

Figure 4:
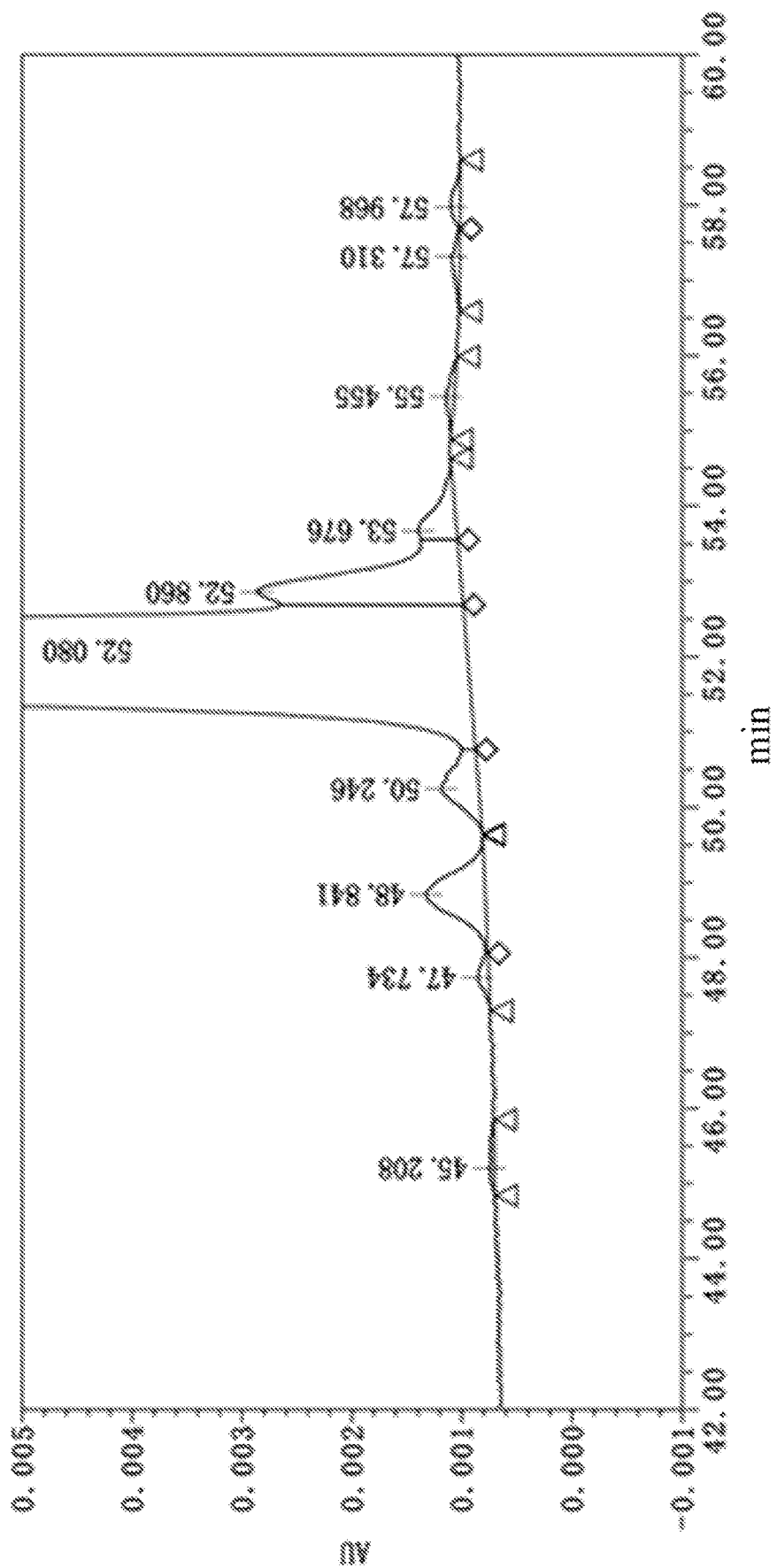
FIG. 4 shows an HPLC spectrum of a refined peptide of liraglutide prepared in comparative example 3.

The crude peptide of liraglutide prepared in comparative example 1 was purified according to the above purification method of Example 9 to obtain 0.47 g of the pure product of liraglutide with a purity of 98.36% and a total yield of 11.34%. The racemate impurity with a structure similar to that of liraglutide, i.e., D-Thr$^5$ liraglutide, was closely adjacent to the main peak, with a relative retention time of about 1.0 and an amount of 1.23%. The HPLC spectrum was shown in FIG. 4. The results of the retention time and peak area of characteristic peaks were shown in Table 5.

TABLE 5

Results of retention time and peak area of characteristic peaks of liraglutide of Comparative Example 3

| Ser. No. | Retention time (min) | Peak area (AU*s) | Peak area ratio % |
|---|---|---|---|
| 1 | 45.208 | 1714 | 0.04 |
| 2 | 47.734 | 2516 | 0.06 |
| 3 | 48.841 | 20819 | 0.46 |
| 4 | 50.246 | 12611 | 0.28 |
| 5 | 52.080 | 4385374 | 97.53 |
| 6 | 52.860 | 55484 | 1.23 |
| 7 | 53.676 | 10013 | 0.22 |
| 8 | 55.455 | 2571 | 0.06 |
| 9 | 57.310 | 2570 | 0.06 |
| 10 | 57.968 | 2576 | 0.06 |

The crude peptide of liraglutide prepared in comparative example 2 was purified according to the above purification method of Example 9 to obtain 0.48 g of the pure product of liraglutide with a purity of 97.53% and a total yield of 12.58%. The racemate impurity with a structure similar to that of liraglutide, i.e., D-Thr$^5$ liraglutide, was closely adjacent to the main peak, with a relative retention time of about 1.0 and an amount of 1.23%. The HPLC spectrum was similar to that shown in FIG. 4.

As can be seen from the HPLC spectra of examples 9 to 15 and comparative example 3, after simple purification steps, D-Thr$^5$ liraglutide among liraglutide had been substantially removed, and its maximum amount is only 0.27% in the refined peptide. However, D-Thr$^5$ liraglutide in the comparative examples is more difficult to remove, which has an amount as high as 1.23% in the refined peptide and is larger than that in the crude peptide prepared by the method of the present disclosure. It can be foreseen that if further purification is carried out in order to reduce the amount of racemate impurity D-Thr$^5$ liraglutide, the lower original yield will be further lowered.

It can be seen that the method of the present disclosure substantially reduces the production of the racemate impurity D-Thr$^5$ liraglutide in the synthesis of liraglutide and ensures the yield of liraglutide. It is advantageous for purifying to obtain the refined peptide of liraglutide with a low content of D-Thr$^5$ liraglutide.

Although the disclosure is illustrated and described herein with reference to specific embodiments, the disclosure is not intended to be limited to the details shown. Rather, various modifications may be made in the details within the scope and range of equivalents of the claims and without departing from the disclosure.

What is claimed is:

1. A process for synthesizing liraglutide with a low racemate impurity comprising:

synthesizing to obtain a propeptide, and then coupling a 2~5 amino acid residue-containing peptide with Thr-Phe to the propeptide by using solid-phase synthesis, further performing a solid-phase synthesis to obtain a liraglutide resin, cleaving the liraglutide resin after side chain modification, or directly cleaving the liraglutide resin, purifying, and lyophilizing to give liraglutide wherein the 2~5 amino acid residue-containing peptide with Thr-Phe is selected from the group consisting of Thr-Phe, Gly-Thr-Phe, Thr-Phe-Thr, Gly-Thr-Phe-Thr (SEQ ID NO:2), Glu-Gly-Thr-Phe (SEQ ID NO:3), Ala-Glu-Gly-Thr-Phe (SEQ ID NO:5), Glu-Gly-Thr-Phe-Thr (SEQ ID NO:6), and Gly-Thr-Phe-Thr-Ser (SEQ ID NO:7).

2. The process according to claim 1, wherein pentapeptide Glu-Phe-Ile-Ala-Trp (SEQ ID NO:9) is used during the process of synthesizing the propeptide.

3. The process according to claim 1, wherein during the process of synthesizing liraglutide, a dipeptide fragment, a tripeptide fragment, a tetrapeptide fragment, a pentapeptide fragment or a combination thereof is coupled to an amino acid and a Fmoc-Gly-resin to obtain the liraglutide resin; wherein:

the dipeptide fragment is selected from the group consisting of His-Ala, Ala-Glu, Glu-Gly, Thr-Ser, and Ala-Ala;

the tripeptide fragment is selected from the group consisting of Glu-Phe-Ile, Ser-Asp-Val, and Thr-Ser-Asp;

the tetrapeptide fragment is selected from the group consisting of Lys-Glu-Phe-Ile (SEQ ID NO:10) and Glu-Phe-Ile-Ala (SEQ ID NO:11);

the pentapeptide fragment is selected from the group consisting of Glu-Phe-Ile-Ala-Trp (SEQ ID NO:12), Ala-Lys-Glu-Phe-Ile (SEQ ID NO:13), Lys-Glu-Phe-Ile-Ala (SEQ ID NO:14), and Ala-Trp-Leu-Val-Arg (SEQ ID NO:15); and two peptide fragments are not used in combination when a same amino acid residue is present at respective ends of the two peptide fragments to be coupled with each other.

4. The process according to claim 3, wherein the combination comprises a combination of one of Glu-Phe-Ile, Lys-Glu-Phe-Ile (SEQ ID NO:10), and Ala-Lys-Glu-Phe-Ile (SEQ ID NO:13) with Ala-Trp-Leu-Val-Arg (SEQ ID NO:15).

5. The process according to claim 1, wherein the 2~5 amino acid residue-containing peptide with Thr-Phe is selected from one of Thr-Phe, Gly-Thr-Phe and Thr-Phe-Thr.

6. The process according to claim 3, wherein the combination comprises Ala-Trp-Leu-Val-Arg (SEQ ID NO:15), Ala-Lys-Glu-Phe-Ile (SEQ ID NO:13), Ser-Asp-Val, and Glu-Gly.

7. The process according to claim 3, wherein the combination comprises Glu-Phe-Ile-Ala-Trp (SEQ ID NO:12), Ala-Ala, Ser-Asp-Val, and Ala-Glu.

8. The process according to claim 3, wherein the combination comprises Ala-Trp-Leu-Val-Arg (SEQ ID NO:15), Glu-Phe-Ile, Thr-Ser-Asp, and Ala-Glu.

* * * * *

SEQUENCE LISTING

```
<160> NUMBER OF SEQ ID NOS: 24

<210> SEQ ID NO 1
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: MISC_FEATURE
<222> LOCATION: (5)..(5)
<223> OTHER INFORMATION: D-threonine
<220> FEATURE:
<221> NAME/KEY: MISC_FEATURE
<222> LOCATION: (20)..(20)
<223> OTHER INFORMATION: Lys linked to N-epsilon-(N-alpha-Palmitoyl-L-
      gamma-glutamyl)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Gly Thr Phe Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 3

Glu Gly Thr Phe
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Thr Phe Thr Ser
1

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Ala Glu Gly Thr Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Glu Gly Thr Phe Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Gly Thr Phe Thr Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Thr Phe Thr Ser Asp
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 9

Glu Phe Ile Ala Trp
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Lys Glu Phe Ile
1

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide

<400> SEQUENCE: 11

Glu Phe Ile Ala
1

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Glu Phe Ile Ala Trp
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Ala Lys Glu Phe Ile
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Lys Glu Phe Ile Ala
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 15

Ala Trp Leu Val Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Ala linked to Fmoc
<220> FEATURE:
<221> NAME/KEY: MISC_FEATURE
<222> LOCATION: (2)..(2)
<223> OTHER INFORMATION: Trp linked to Boc
<220> FEATURE:
<221> NAME/KEY: MISC_FEATURE
<222> LOCATION: (5)..(5)
<223> OTHER INFORMATION: Arg linked to Pbf

<400> SEQUENCE: 16

Ala Trp Leu Val Arg
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Ala linked to Fmoc
<220> FEATURE:
<221> NAME/KEY: MISC_FEATURE
<222> LOCATION: (2)..(2)
<223> OTHER INFORMATION: Lys linked to Alloc
<220> FEATURE:
<221> NAME/KEY: MISC_FEATURE
<222> LOCATION: (3)..(3)
<223> OTHER INFORMATION: Glu linked to OtBu

<400> SEQUENCE: 17

Ala Lys Glu Phe Ile
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Glu linked to Fmoc and OtBu
<220> FEATURE:
<221> NAME/KEY: MISC_FEATURE
<222> LOCATION: (5)..(5)
<223> OTHER INFORMATION: Trp linked to Boc

<400> SEQUENCE: 18

Glu Phe Ile Ala Trp
1               5

<210> SEQ ID NO 19
```

```
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Lys linked to Fmoc and Alloc
<220> FEATURE:
<221> NAME/KEY: MISC_FEATURE
<222> LOCATION: (2)..(2)
<223> OTHER INFORMATION: Glu linked to OtBu

<400> SEQUENCE: 19

Lys Glu Phe Ile Ala
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Thr linked to Fmoc and tBu
<220> FEATURE:
<221> NAME/KEY: MISC_FEATURE
<222> LOCATION: (3)..(3)
<223> OTHER INFORMATION: Thr linked tBu
<220> FEATURE:
<221> NAME/KEY: MISC_FEATURE
<222> LOCATION: (4)..(4)
<223> OTHER INFORMATION: Ser linked tBu

<400> SEQUENCE: 20

Thr Phe Thr Ser
1

<210> SEQ ID NO 21
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Lys linked to Fmoc and Alloc
<220> FEATURE:
<221> NAME/KEY: MISC_FEATURE
<222> LOCATION: (2)..(2)
<223> OTHER INFORMATION: Glu linked to OtBu

<400> SEQUENCE: 21

Lys Glu Phe Ile
1

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Gly linked to Fmoc
<220> FEATURE:
<221> NAME/KEY: MISC_FEATURE
<222> LOCATION: (2)..(2)
```

```
<223> OTHER INFORMATION: Thr linked to tBu
<220> FEATURE:
<221> NAME/KEY: MISC_FEATURE
<222> LOCATION: (4)..(4)
<223> OTHER INFORMATION: Thr linked to tBu

<400> SEQUENCE: 22

Gly Thr Phe Thr
1

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Glu linked to Fmoc and OtBu
<220> FEATURE:
<221> NAME/KEY: MISC_FEATURE
<222> LOCATION: (3)..(3)
<223> OTHER INFORMATION: Thr linked to tBu
<220> FEATURE:
<221> NAME/KEY: MISC_FEATURE
<222> LOCATION: (5)..(5)
<223> OTHER INFORMATION: Thr linked to tBu

<400> SEQUENCE: 23

Glu Gly Thr Phe Thr
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Gly linked to Fmoc
<220> FEATURE:
<221> NAME/KEY: MISC_FEATURE
<222> LOCATION: (2)..(2)
<223> OTHER INFORMATION: Thr linked to tBu
<220> FEATURE:
<221> NAME/KEY: MISC_FEATURE
<222> LOCATION: (4)..(4)
<223> OTHER INFORMATION: Thr linked to tBu
<220> FEATURE:
<221> NAME/KEY: MISC_FEATURE
<222> LOCATION: (5)..(5)
<223> OTHER INFORMATION: Ser linked to tBu

<400> SEQUENCE: 24

Gly Thr Phe Thr Ser
1               5
```